United States Patent [19]

Carlson

[11] Patent Number: 4,807,612

[45] Date of Patent: Feb. 28, 1989

[54] PASSIVE EAR PROTECTOR

[75] Inventor: Elmer V. Carlson, Prospect Heights, Ill.

[73] Assignee: Industrial Research Products, Inc., Elk Grove Village, Ill.

[21] Appl. No.: 118,455

[22] Filed: Nov. 9, 1987

[51] Int. Cl.$^4$ .............................................. A61F 11/02
[52] U.S. Cl. ...................................... 128/868; 381/74; 381/158; 381/157
[58] Field of Search ................ 128/152; 181/129, 130, 181/132, 175; 183/23.1, 25, 68.6, 69, 158, 159, 183, 187; 381/74, 158, 187

[56] References Cited

U.S. PATENT DOCUMENTS

| | | | |
|---|---|---|---|
| 1,016,877 | 2/1912 | Elliott | 128/152 |
| 1,148,849 | 8/1915 | Mallock | 128/152 |
| 1,279,396 | 9/1918 | Michelson et al. | 128/152 |
| 1,599,961 | 9/1926 | Hall et al. | 181/129 |
| 2,361,963 | 11/1944 | Rosenblatt | 381/158 |
| 2,363,175 | 11/1944 | Grossman | 381/187 |
| 2,476,224 | 7/1949 | Rosenblatt | 128/152 |
| 2,487,038 | 11/1949 | Baum | 128/152 |
| 3,134,456 | 5/1964 | Wadsworth | 181/129 |
| 4,540,063 | 9/1985 | Ochi et al. | 128/152 |
| 4,644,581 | 2/1987 | Sapiejewski | 381/74 |

Primary Examiner—Robert A. Hafer
Assistant Examiner—Charles H. Sam
Attorney, Agent, or Firm—Wallenstein, Wagner, Hattis & Strampel, Ltd.

[57] ABSTRACT

A passive ear protector device for positioning in the ear of the user for protecting the ear from sounds of high intensity. The device attenuates sound in a manner which tends to preserve the natural quality of the incoming sound, in particular with respect to the natural resonance of the ear canal.

16 Claims, 2 Drawing Sheets

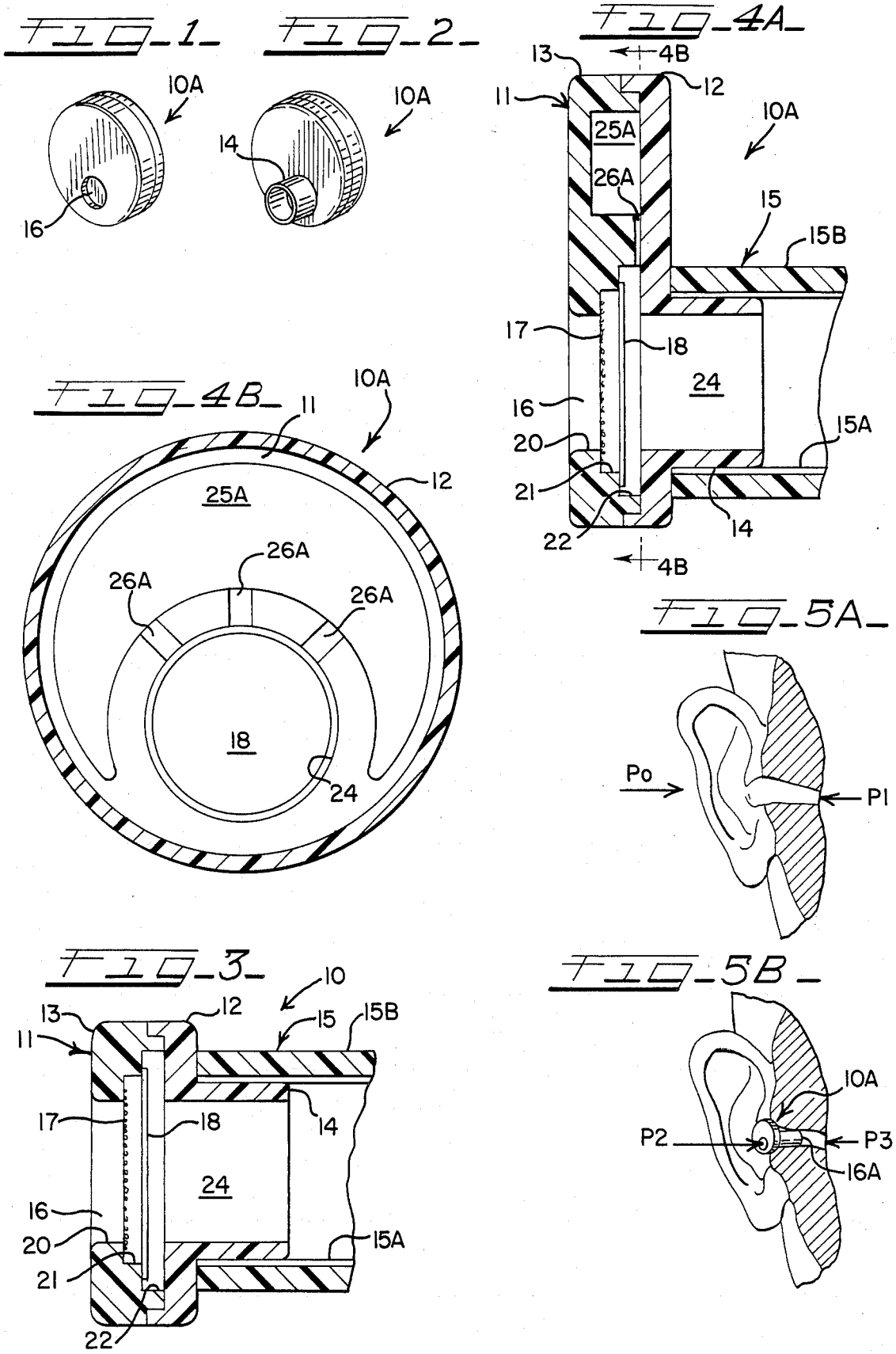

FIG-6-
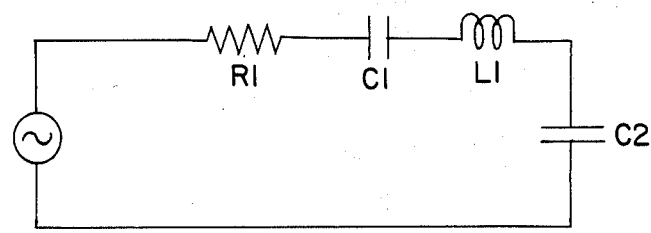
FIG-7-
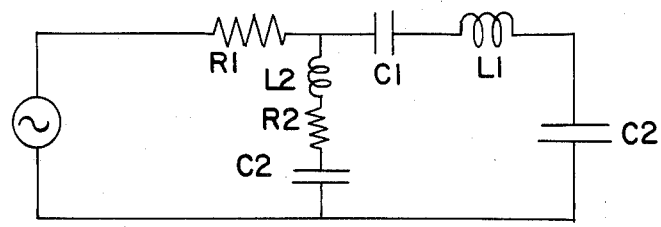
FIG-8-
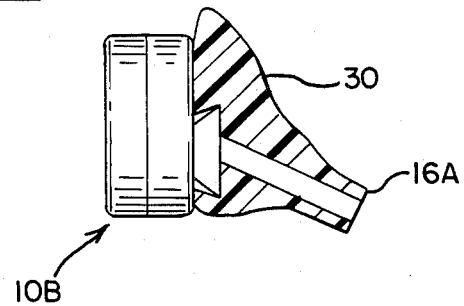

4,807,612

PASSIVE EAR PROTECTOR

DESCRIPTION

1. Technical Field

The technical field of the invention is hearing protection devices for high noise environments.

2. Background Art

Ear plugs for reducing the level of transmitted sound by providing an obstruction of the ear canal sound path are well known. Most prior art ear plugs tend to distort reception of normal sound. Some attempts have heretofore been made to provide ear plugs for selectively attenuating the incoming sound; for example, see U.S. Pat. No. 3,565,069 to R. N. Miller for an Acoustical Filter Device and U.S. Pat. No. 3,637,040 to A. G. Gorman for Ear Defenders. The Miller U.S. Pat. No. 3,565,069 states that the filter device disclosed therein screens out substantially all noise above a predetermined level while permitting sound below a such level to pass therethrough without deleterious loss. The Gorman U.S. Pat. No. 3,637,040 notes that sounds to the wearer's ear are substantially unattenuated within a chosen frequency range and that all sounds and noises which are not within the frequency range which are necessary for the transmission of intelligible speech are eliminated.

In the particular case of ear plugs designed for insertion into the ear canal, a normal ear canal transmission resonance at approximately 2.7 kilohertz is effectively suppressed, thereby effectively suppressing by a greater amount a significant portion of the 1–3 kilohertz information. Moreover, the act of inserting such an ear plug into the ear canal also normally introduces a spurious transmission of pre-emphasis in the 5–8 kilohertz region. It is desirable in an attenuating ear plug that the 2.7 kilohertz resonance be restored, and that the 5–8 kilocycle spurious emphasis be compensated for. To Applicant's knowledge, neither of these objections have previously been accomplished in a purely passive ear device.

U.S. Pat. No. 3,985,960, issued to Wallace, describes an electrically driven electromechanical transducer fitted into an earplug having, in one version, various acoustical elements disposed therein to provide at the eardrum a frequency response characteristic tailored to represent that of the unobstructed ear canal. This is, however, not an attenuator, but an attempt to produce a form of high-fidelity earphone. Thus, the Wallace patent describes a device that is neither passive or coupled to the outside air. To Applicant's knowledge, there exists no simple passive earplug-type attenuator properly compensated to correct for the upset in the transfer characteristics of the ear canal arising from an earplug inserted at the outer end thereof.

SUMMARY OF THE INVENTION

The inventive ear protector comprises a passive attenuating device adapted to be inserted into the outer ear canal of the human ear, and includes an acoustical attenuating network for attenuating incoming sound without distorting the quality of the sound. According to a feature of the invention, the attenuating network restores the necessary 2.7 kilohertz pre-emphasis of the open-ear canal so as to improve the intelligibility of human speech.

The invention provides an improved acoustical attenuating device comprising an ear protector which utilizes a combination of acoustical elements related and connected to provide a substantial sound attenuation throughout a wide range of audio frequencies. The device has response characteristics which are comparable with that of the anatomical structures of the human ear so that the attenuated sound reaching the inner ear through the ear protector has substantially the same characteristics as the sound which would normally be received by the user's ear if no ear protector were present, but is of a reduced amplitude level. According to a further feature of the invention, an auxiliary resonator is provided for the disclosed passive ear protector for removing an undesired eight kilohertz transmission peak which occurs because of the acoustical obstructing action of the ear plug in the ear canal.

Further features of the invention will be readily apparent from the following detailed description of preferred embodiments, when considered in conjunction with the drawings, wherein:

BRIEF DESCRIPTION OF DRAWINGS

FIG. 1 is an isometric view of an advanced form of the passive ear protector in accordance with the invention;

FIG. 2 is an isometric view of the structure of FIG. 1 rotated approximately 180°;

FIG. 3 is a relatively enlarged cross-sectional view of a simple version of the ear protector of FIG. 1;

FIG. 4A is a cross-sectional view of the advanced version of the invention shown in FIGS. 1 and 2;

FIG. 4B is a partially-cutaway rear view of the ear protector shown in FIG. 4A;

FIGS. 5A and 5B are sketches of a human ear structure useful in explaining the features of the present invention;

FIG. 6 is a an equivalent circuit of the ear protector of FIG. 3 inserted into the ear canal;

FIG. 7 is an equivalent circuit of the ear protector of FIG. 4A and FIG. 4B inserted into the ear canal; and, FIG. 8 is a partial cross-sectional view showing the ear protector affixed to an ear mold;

DETAILED DESCRIPTION

While this invention is susceptible of embodiment in many different forms, there is shown in the drawings and will herein be described in detail a preferred embodiment of the invention with the understanding that the present disclosure is to be considered as an exemplification of the principles of the invention, and is not intended to limit the broad aspect of the invention to the embodiments illustrated.

It has been found that in many situations where the ambient sound level is of sufficient intensity to be uncomfortable or hazardous to the hearing of an individual, such as the high sound or noise level developed in industrial plants, or such as due to explosion noise, a tolerable or non-hazardous situation can be realized by attenuating the sound by some moderate amount of between 10 to 30 dB. Accordingly, the invention is directed to a passive device for attenuating the incoming sound somewhat while yet affording the normal individual sufficient hearing range so that when he is not in the intense sound environment he can still carry on normal conversations and receive the normal environmental sounds essential to his comfort and safety. For example, a 95 dB SPL (Sound Pressure Level) noise ambient is normally acceptable if the noise transmitted into the ear can be attenuated only to 75 dB SPL. Accordingly, a person with normal hearing may wear the inventive protector in a 95 dB SPL environment to lower the input level to his ear desired to 75 dB SPL with comfort and safety. Yet, when that person emerges from the high noise level environment, the protector will not seriously handicap his hearing in the more normal surroundings.

Refer now to FIGS. 1–8. The inventive passive ear protector 10 is structured, designed and dimensioned to be carried in an ear of the user, and, in a simple embodiment, the housing 11 of ear protector 10 (FIG. 3) is approximately 0.5 inch in diameter and 0.10 inch in thickness. Housing 11 is thus circular in plan view and is rectangular in side view. The outer or input side of an advanced form of the protector is best seen in FIG. 1, and the inner or output side of the protector is best seen in FIG. 2. An input sound port 16 is formed on the outer side of protector 11 and a sound tube 14 extends from the inner side of the protector.

The housing 11, which may be of a plastic such as cellulose acetate butyrate, comprises a base portion 12 and a mating cap portion 13. The acoustical conduit or sound passage 24 comprising the tube 14 extends outwardly from base 12, i.e., from the inner side of housing 11 and is insertible into the user's ear canal; note, FIG. 5B. FIG. 8 shows an alternative embodiment configured for snapin engagement with an ear mold 30. In one embodiment, tube 14 is approximately 0.5 inches in length and 0.125 inch in diameter.

An insert tube 15, as shown in FIGS. 3 and 4A, of compressible flexible material is provided. The insert tube 15 includes a core 15A which is sufficiently rigid to enable insert tube 15 to retain its shape, but which is sufficiently flexible to bend to conform to the ear canal, as indicated in FIG. 5B. Core 15A is of a diameter to fit snugly onto sound tube 14. The outer portion 15B of tube 15 is of a compliant material and fits into the ear canal in close conforming relation therewith to provide a sealing acoustical interface with the ear canal to prevent external sound from passing around the exterior surface of housing 11 into the ear canal. The sound output portion 16A is indicated in FIG. 5B as the open or interior end of tube 15. Insert tube 15 is readily removable from sound tube 14, such as for cleaning or replacement. The replaceability of insert tube 15 increases the hygienic acceptability of the ear protector to the user.

The sound input port 16, through which the sound enters the ear protector 10, is formed in cap portion 13, i.e., in the outer side of the housing 11. A damping element or member 17, such as perforated screen or cloth, extends across the input port 16 to provide a suitable acoustical resistance to sound entering the ear protector 10. Positioning of the damping member 17 toward the outer side of housing 11, as shown in FIG. 3, tends to protect member 17 from contamination from ear secretion. Note, however, that damping member 17 may also be located adjacent the inner end of tube 14. A flexible diaphragm 18 is positioned across the sound passage or passageway 14 in spaced relation to the damping member 17.

In the embodiment shown, the input port 16 and passage 24 comprises a cavity 20 with an entrance approximately 0.125 inch in diameter. A second bore 21 of slightly larger diameter forms a second cavity and a third bore 22 of still slightly larger diameter forms a third cavity. A pressure-dividing complaint diaphragm 18 is disposed on the shoulders defining bore 21 as shown. The different diameter bores form steps or shoulders, and the damping element 17 and diaphragm 18 are conveniently mounted in position, such as by adhesively bonding them to the respective shoulders. The cavities formed by bores 21 and 22 are quite small and do not have significant acoustical effect in the operation of the ear protector 10.

As is known, in operation, diaphragm 18 vibrates or moves in response to external sound pressure impinging thereon. Diaphragm 18 couples the sound pressure through the sound passage 24 and tube 14 to the eardrum cavity indicated in FIG. 5B.

As mentioned above, the natural resonance of the ear canal shapes the frequency-amplitude characteristic of the sound pressure delivered to the eardrum, and when the ear is obstructed by an attenuating plug, the natural resonance in the ear canal is significantly altered. Accordingly, a feature of the present invention is to provide an acoustical network for reconstructing this natural resonance-dependent relationship when a protector is positioned in the user's ear canal.

Consider now the following sound pressure relations and refer particularly to FIGS. 5A and 5B wherein the following relations are established:

$P_0$ is the ambient sound wave pressure;

$P_1$ is the sound pressure at the eardrum with the ear unobstructed;

$P_2$ is the sound pressure at the outer surface of an attenuating plug with the ear obstructed, i.e., with an ear plug placed in the ear; and, $P_3$ is the sound pressure at the eardrum with the ear obstructed.

To preserve the natural quality of the sound wave pressure $P_0$, the ratio $P_3/P_1 = a_1$ should be constant at all useful frequencies. The amount of sound attenuation is given by the relation $A = 20 \log_{10}(a_1)$ decibels.

To make "$a_1$" a constant, the attenuation ratio of the plug given by $P_3/P_2 = a_2$ must have a specific value which is a function of frequency. The proper value is found experimentally by taking the measurements $P_1/P_0 = a_3$; and, $P_2/P_0 = a_4$ and then taking their ratio:

$$a_3/a_4 = (P_1/P_0)/(P_2/P_0) = P_1/P_2 = a_5$$

If the attenuation ratio of the plug "$a_2$" is set as "$a_5$" multiplied by a constant, "$a_6$", that is, if:

$a_2 = a_5 \times a_6$ then, $a_2 = (P_1/P_2) \times a_6$; or.

$(P_3/P_2) = (P_1/P_2) \times a_6$ and hence $a_6 = (P_3/P_1)$, and $a_1 = P_3/P_1$ Thus, it can be seen that $$a_1 = a_6 = \frac{\text{eardrum sound pressure, obstructed}}{\text{eardrum sound pressure, unobstructed}}$$

The pressure in the plugged or obstructed ear is thus the same as the pressure in the clear or unobstructed ear but reduced by a constant factor.

A rearranging of the foregoing relations establishes that the proper value of the attenuation ratio is given by $a_2 = a_5 \times a_1$.

The stiffness of the diaphragm 18 in the inventive passive ear protector 10 is selected so that the diaphragm 18 reduces the pressure developed on the inner or ear side of the diaphragm 18 by the desired attenuation factor ($a_2$). At frequencies well below the resonance of the diaphragm, stiffness is the principal constraint of the diaphragm motion; and at these lower frequencies, the diaphragm, in conjunction with the stiffness of the air in the ear canal and the passage 24 leading to the ear canal, functions as a pressure divider. The diameter and length of the passage 24, including tubing 14, the compliance and mass of the diaphragm 18 and the resistance of the damping member 17 are selected to provide a maximum of transmission (resonance) at the frequencies at which the ear normally enhances the pressure at the eardrum relative to the pressure in the incoming sound.

The invention addresses two principal concepts. First, since the sound attenuating plug represents generally an acoustical compliance, at least at the lower frequencies, an attenuator is constructed by interposing a compliance near the entrance of the ear canal to form a pressure divider. Second, when the ear is obstructed by an attenuating plug, the natural resonance in the ear canal, which shapes the frequency-amplitude characteristic of the sound pressure delivered to the eardrum, is altered. The invention provides appropriate acoustical networks for reconstructing the natural frequency dependent relationship of the human ear unobstructed.

In the inventive structure, the compliance of the diaphgram 18 in combination with the occluded volume of passages 24 forms an attenuator having the nominal attenuation of the protector. The diameter and length of the tube 15, the compliance of the diaphragm 18 and resistance in damping member 17 are chosen to provide a maximum of transmission (resonance) at the frequency at which the ear normally enhances the pressure at the eardrum relative to the pressure in the arriving sound wave. This natural resonance is destroyed by inserting a sealing plug into the ear canal, as will be discussed below. The value of the damping element 17 is chosen so that enhancement has the amplitude which preserves the frequency characteristic (or resonance) that the eardrum normally experiences. Thus, the sound delivered to the eardrum is substantially that which would have been observed at the eardrum in the absence of the attenuator, but it is decreased by a constant factor, for instance, to 10% of the unattenuated eardrum sound pressure for a plug rated at 20 dB attenuation.

The foregoing description has dealt with an embodiment of the invention designed to overcome one basic problem inherent in any sound-transmission system inserted into the ear. The human ear canal is an open-ended device, and thus has one basic property of an open-ended acoustical structure, namely, the inherent property of producing a transmission resonance. Thus, taking the length of a typical human ear canal as being approximately 2.5 to 2.8 cm, one readily computes from the theory of the closed-ended organ pipe that the fundamental resonant frequency would be approximately 3.2 kilohertz. Because the ear canal is extended at the open end by the concha and terminated at the other end by the less than rigid eardrum, the observed resonant frequency is near 2.7 kilohertz. A basic requirement of faithful auditory reproducibility is that with the ear protector inserted into the ear, this general resonance must be maintained.

On the other hand, insertion of a sealing aperture of any form into the ear canal has the general effect of transforming the ear canal into an essentially closed resonator. The previously-mentioned 2.7 kilohertz resonance is an inherent property of the unobstructed ear canal. By quite elementary methods, one may show that placing a significant obstruction at the outer end of the ear canal effectively destroys this resonance. The previously-described embodiment restores this resonance to the transmission properties of the system, as may be seen with reference to an equivalent circuit of the ear with the ear protector in place, as shown in FIG. 6.

As previously mentioned, placing the compliant member 18 in the acoustical passage has the generally effect of providing a pressure-dividing actions with respect to the ear canal. Thus, in FIG. 6, this pressure-dividing action is shown in schematic form as a division between capacitors C1 and C2. Here C2 represents the compliance (reciprocally related to "stiffness") of the residual volume of the ear canal, and C1 represents the compliance of the diaphragm 18. Such a pressure-divider will serve as an attenuator; however, it will not restore the missing 2.7 kilohertz resonance. This is supplied by the resistance R1 of the damping element 17, having a resistance of 125 acoustical ohms, and an acoustical inductance L1 derived from the total bore extending from the compliant diaphargm 18 to the tip of the ear mold 16A. The parameters L1 and R1 are, within wide limits, independently adjustable, and in the present invention serve to substantially restore the 2.7 kilohertz resonance and the appropriate breadth thereof.

It is equally evident that the capacitor C1 and resistor R1, shown in FIG. 6, could be interchanged, i.e., the position of the damping element 17 and the diaphragm 18 could be interchanged, if desired, without effecting the general properties of the system described above. The compliant diaphragm 18 has an acoustic compliance of 0.25 acoustic microfarads, and the total bore represented by conductor L1 is about 12.8 mm long and 3.6 mm in diameter.

A preferred embodiment of the invention not only retains the foregoing feature, but also deals with the spurious resonance that arises from sealing the outer end of the ear canal, namely, that the structure interior to the membrane 18 then approximates a closed acoustical chamber.

It has been determined by measurements of the changes in the sound pressure thresholds of hearing in human subjects with and without devices of the type just described, and also by measurements on an electrical analog circuit model of the device including the ear canal, that a resonance or increase in transmission occurs at about 8 kilohertz. When the device is inserted in the ear, a major discontinuity in the sound transmission path is created at the end of the device portion that is inserted into the ear. The remainder of the ear canal that is between this end and the ear drum is an acoustic transmission line of a different characteristic impedance than that of the passage 24. It is believed that this discontinuity and the lengths of the acoustic transmission paths are responsible for such disturbance in the transmission. Thus, inserting the ear protector into the ear canal introduces a spurious 8 kilohertz transmission-augmenting resonance which should preferably be eliminated.

Refer now to FIGS. 4A and 4B, which show an alternative embodiment of the inventive passive ear protector 10A. Identical element numbering is used for elements having identical function with respect to those shown in the previously-described embodiment. The ear protector 10A is substantially identical to ear protector 10, but includes damping apertures or slits 26A which couple sound from passages 24 to an auxiliary chamber 25A to form an auxiliary acoustic branch. The apertures 26A form resistive-inductive damping elements.

As discussed above, the simpler ear protector 10 provides a damping element 17 and a diaphragm 18 positioned in the sound conveying passage or duct 24 to produce a first correction to the transmission characteristic of the device. In addition to the foregoing, the improved passive ear protector 10A further improves and smooths out the output provided by the invention. More specifically, the impedance of the auxiliary acoustic chamber 25A and the apertures 26A tends to enable the passive ear protector to provide an output which minimizes spurious amplitude fluctuations or peaks in the operating frequency range. A theory of operation of such an auxiliary branch is described in U.S. Pat. No. 4,006,321 to E. V. Carlson, entitled "Transducer Coupling System", and assigned to the same Assignee as the present invention.

The parameters of the apertures 26A and the auxiliary chamber 25A are selected such that the effective acoustic impedance in the frequency range of the excess transmission causes a lowering of the amount of sound transmitted. The invention thus provides structures for attenuating incoming sound by a selected amount while retaining the natural quality of the sound throughout the operating frequency range.

This is best seen with reference to the equivalent circuit shown in FIG. 7. Here the extra branch constitutes a series-resonant shunt circuit having elements L2, R2 representing the mass of the air in passages 26A and the flow resistance therein arising from viscous drag. Capacitor C2 represents the compliance of the cavity 25A, this cavity having a volume of 0.01 cubic cm. Each passage 26A is 0.28 mm long in the direction of flow and is 0.36 mm×0.08 mm in cross section. Again, referring to FIG. 7, it is clear that the strength of this shunting action, and hence the suppression of transfer of 8 kilohertz information to the ear canal, is set by R2, and that the frequency at which this shunting action is maximized will to first order be set by the magnitudes of inductor L2 and capacitor C2. Here again, these parameters are generally independently adjustable to provide the desired correction. It will further be appreciated that elements L2, R2, C2 could equally well be connected to shunt the juncture of elements C1 and R1, provided that the magnitudes of elements L2, R2 and C2 are appropriately adjusted.

While the specific embodiments have been illustrated and described, numerous modifications come to mind without significantly departing from the spirit of the invention and the scope of protection is only limited by the scope of the accompanying claims.

I claim:

1. A passive ear protector positionable in the canal of a user's ear for attenuating incoming sound, said protector comprising in combination sound input and output ports, a sound passage coupling said ports, and first attenuation-correcting means for providing a maximum of transmission for at least one frequency at which the unobstructed ear canal normally enhances the pressure at the eardrum and at which the presence of said ear protector in said canal substantially reduces said transmission to produce a spectrum of the sound coupled through the ear protector to the user's ear which is substantially the same at said one frequency as that which would be effective at the user's ear in the absence of the passive ear protector, but decreased by a substantially constant factor, said attenuation-correcting means including complaint diaphargm means positioned across said passage for responding to incoming sound and providing attenuated sound pressure communication through said passage to the user's ear, said diaphragm means being configured to function as a pressure divider with the occluded volume of said ear canal, and a damping member positioned across said sound passage, said first attenuation-correction means being the configuration of said diaphragm, said sound passage and said damping member to provide said transmission maximum.

2. A passive ear protector as in claim 1, wherein the compliance of the diaphragm, the cross-section dimensions and length of the sound passage and the resistance of the damping element are chosen to form a frequency-corrected attenuator providing at the lower audio frequencies a response at the eardrum having generally the same frequency characteristic as the user's unoccluded ear.

3. A passive ear protector as in claim 1, wherein said sound passage comprises a relatively elongated tube and wherein the length of the tube and compliance of the diaphragm are chosen to resonate at the frequency at which the unobstructed ear canal normally enhances the pressure at the eardrum.

4. A passive ear protector as in claim 1, 2, or 3, further including second attenuation-correcting means for producing selectively augmented attenuation at the frequency of at least one sound-emphasizing resonance caused by the presence of said ear protector in said canal, said second attenuation-correcting means including an auxiliary acoustical branch comprising an auxiliary acoustic chamber and at least one acoustical impedance element coupling sound from said sound passage to said auxiliary chamber, said auxiliary branch being configured to provide a resonating energy-absorbing action at said at least one sound-emphasizing resonant frequency.

5. A passive ear protector as in claim 4, wherein said acoustic impedance elements comprise slits formed between the auxiliary chamber and the sound passage.

6. A passive sonic attenuator for insertion into the ear canal comprising:
  plug means for occludingly sealing the outer portion of said ear canal;
  port means for passing external sound through said plug means and into said ear canal;
  attenuator means associated with said port means for attenuating the sound passing therethrough over a spectrum of audible frequencies; and
  first acoustical attenuation-modifying means acoustically communicating with said port means for substantially reducing said attenuation with respect to that of adjacent portions of said spectrum in the vicinity of 2.7 kilohertz sufficiently to generally reproduce for transmission into said ear canal a sound spectrum having the normal 2.7 kilohertz transmission-augmenting pre-emphasis of an unoccluded ear canal.

7. The sonic attenuator of claim 6 further including second acoustical attenuation-modifying means acoustically communicating with said port means for selectively increasing said attenuation at the frequency of at least one sound-emphasizing resonance produced by the occulsion of said ear canal by the insertion of said attenuator.

8. The sonic attenuator of claim 7 wherein said port means includes input port means disposed to capture ambient sound with said attenuator so inserted, output port means disposed to communicate directly with the interior of said ear canal, and main passage means acoustically communicating between said input and output port means, said attenuator including compliant diaphragm means and first acoustical damping means disposed across said main passage means, said main passage means including elongated conduit means acoustically communicating between said output port means and one of said diagphragm means and said first damping means, said first attenuation-modifying means including the resistance of said damping means, the compliance of said diaphragm means, and the inertance governed by the dimensions of said elongated conduit means chosen to provide a transmission-augmenting resonance in the general region of 2.7 kilohertz.

9. The sonic attenuator of claim 8 wherein said second attenuation-modifying means includes acoustical resonating means and branch port means acoustically communicating between said acoustical resonating means and said main passage means.

10. The sonic attenuator of claim 9 wherein said second attenuation-modifying means includes at least one acoustical chamber of given volume and at least one sound-diverting branch passageway of given length and given cross-section acoustically communicating between said main passage means and said chamber, and includes said volume of said chamber and said length and cross-section of said branch passageway chosen to form a frequency-resonant acoustical network diverting acoustical energy from said main passage means to provide said selectively increased attenuation at said at least one sound-emphasizing resonant frequency.

11. The sonic attenuator of claims 8, 9, or 10 wherein said diaphragm means is placed between said first acoustical damping means and said output port means.

12. The sonic attenuator of claim 10 wherein said branch passageway is acoustically coupled to said main passageway at a point between said diaphragm means and the major portion of said elongated passage means.

13. The sonic attenuator of claim 11 wherein said branch passageway is acoustically coupled to said main passageway at a point between said diaphragm means and the major portion of said elongated passage means.

14. The sonic attenuator of claim 6 wherein said port means includes input port means disposed to capture ambient sound with said attenuator so inserted, output port means disposed to communicate directly with the interior of said ear canal, and main passage means acoustically communicating between said input and output port means, said attenuator including compliant diaphragm means and first acoustical damping means disposed across said main passage means, said main passage means including elongated conduit means acoustically communicating between said output port means and one of said diaphragm means and said first damping means, said first attenuation-modifying means including the resistance of said damping means, the compliance of said diaphragm means, and the dimensions of said elongated conduit means chosen to provide a transmission-augmenting resonance in the general region of 2.7 kilohertz.

15. The sonic attenuator of claims 9, 10, 11, 12, 13, or 14 wherein said selectively increased attenuation is provided at a frequency of approximately 8 kilohertz.

16. The sonic attenuator of claim 13 wherein said at least one branch passageway includes a plurality of slits acoustically communicating between said main passage means and said chamber.

* * * * *